(12) United States Patent  (10) Patent No.: US 9,106,270 B2
Puterbaugh et al.  (45) Date of Patent: Aug. 11, 2015

(54) TRANSMITTING DATA ACROSS A PATIENT ISOLATION BARRIER USING AN ELECTRIC-FIELD CAPACITIVE COUPLER MODULE

(71) Applicant: COVIDIEN LP, Mansfield, MA (US)

(72) Inventors: Lewis Puterbaugh, Longmont, CO (US); Jeffrey L. Jensen, Boulder, CO (US)

(73) Assignee: Covidien LP, Mansfield, MA (US)

( * ) Notice: Subject to any disclaimer, the term of this patent is extended or adjusted under 35 U.S.C. 154(b) by 53 days.

(21) Appl. No.: 14/022,535

(22) Filed: Sep. 10, 2013

(65) Prior Publication Data

US 2014/0094120 A1  Apr. 3, 2014

Related U.S. Application Data

(60) Provisional application No. 61/708,990, filed on Oct. 2, 2012.

(51) Int. Cl.
*H04B 1/38* (2006.01)
*H04B 5/00* (2006.01)
*A61B 18/12* (2006.01)

(52) U.S. Cl.
CPC .......... *H04B 5/0025* (2013.01); *A61B 18/1206* (2013.01); *H04B 5/005* (2013.01); *H04B 5/0012* (2013.01)

(58) Field of Classification Search
USPC .............. 455/41.1, 41.2, 41.3, 515, 574, 572; 600/407, 544, 509, 545, 301, 111, 476, 600/564, 309, 483
See application file for complete search history.

(56) References Cited

U.S. PATENT DOCUMENTS

| | | | |
|---|---|---|---|
| 5,300,068 A | 4/1994 | Rosar et al. | |
| 5,452,725 A | 9/1995 | Martenson | |
| 5,531,774 A | 7/1996 | Schulman et al. | |
| 5,562,720 A | 10/1996 | Stern et al. | |
| 5,870,046 A | 2/1999 | Scott et al. | |
| 6,809,508 B2 | 10/2004 | Donofrio | |
| 6,977,495 B2 | 12/2005 | Donofrio | |
| 7,120,245 B2* | 10/2006 | Knubben et al. ......... | 379/399.01 |
| 7,396,336 B2 | 7/2008 | Orszulak et al. | |
| 8,096,961 B2 | 1/2012 | Orszulak et al. | |
| 8,660,489 B2* | 2/2014 | Barrenscheen et al. ..... | 455/41.2 |
| 2005/0149151 A1* | 7/2005 | Orszulak et al. ................ | 607/96 |

(Continued)

FOREIGN PATENT DOCUMENTS

| | | |
|---|---|---|
| EP | 1810631 A2 | 7/2007 |
| EP | 1990020 A2 | 11/2008 |

(Continued)

OTHER PUBLICATIONS

"Capacitive Coupling Simplifies Isolation, Electronics", VNU Business Publications, vol. 59, No. 37 (Dec. 1, 1986).

(Continued)

*Primary Examiner* — Ganiyu A Hanidu (57) ABSTRACT

An electric-field capacitive coupler module includes a first processing unit, a first communication interface coupled to the first processing unit, a second communication interface, and an electric-field capacitive coupler that defines an isolation barrier. The electric-field capacitive coupler apparatus is coupled between the first communication interface and the second communication interface.

11 Claims, 9 Drawing Sheets

(56) References Cited

U.S. PATENT DOCUMENTS

| | | |
|---|---|---|
| 2007/0173802 A1 | 7/2007 | Keppel |
| 2008/0181316 A1* | 7/2008 | Crawley et al. ............... 375/258 |
| 2008/0281311 A1* | 11/2008 | Dunning et al. ................ 606/32 |
| 2009/0018429 A1* | 1/2009 | Saliga et al. .................. 600/407 |
| 2010/0057076 A1 | 3/2010 | Behnke et al. |
| 2011/0087213 A1 | 4/2011 | Messerly et al. |
| 2011/0213355 A1* | 9/2011 | Behnke, II ..................... 606/33 |
| 2012/0116268 A1 | 5/2012 | Orszulak et al. |
| 2013/0197503 A1 | 8/2013 | Orszulak |

FOREIGN PATENT DOCUMENTS

| | | |
|---|---|---|
| EP | 2033588 A1 | 3/2009 |
| WO | 03003680 A1 | 1/2003 |

OTHER PUBLICATIONS

European Search Report, Application No. 13187072.7 dated Feb. 21, 2014.

\* cited by examiner

TRANSMITTING DATA ACROSS A PATIENT ISOLATION BARRIER USING AN ELECTRIC-FIELD CAPACITIVE COUPLER MODULE

CROSS REFERENCE TO RELATED APPLICATION

The present application claims the benefit of and priority to U.S. Provisional Application Ser. No. 61/708,990, filed on Oct. 2, 2012, the entire contents of which are incorporated herein by reference.

BACKGROUND

1. Technical Field

The present disclosure relates to electrosurgical systems. More particularly, the present disclosure relates to systems, apparatus and methods for isolated data transfer using an electric-field capacitive coupler.

2. Discussion of Related Art

Electrosurgical instruments have become widely used by surgeons. Electrosurgery involves the application of thermal and/or electrical energy to cut, dissect, ablate, coagulate, cauterize, seal or otherwise treat biological tissue during a surgical procedure. Electrosurgery is typically performed using a handpiece including a surgical instrument (e.g., end effector, ablation probe, or electrode) adapted to transmit energy to a tissue site during electrosurgical procedures, an electrosurgical generator operable to output energy, and a cable assembly operatively connecting the surgical instrument to the generator. The basic purpose of both monopolar and bipolar electrosurgery is to produce heat to achieve the desired tissue/clinical effect.

In monopolar electrosurgery, devices use an instrument with a single, active electrode to deliver energy from an electrosurgical generator to tissue, and a patient return electrode or pad that is attached the patient (e.g., a plate positioned on the patient's thigh or back) as the means to complete the electrical circuit between the electrosurgical generator and the patient. When the electrosurgical energy is applied, the energy travels from the exposed or active electrode, to the surgical site, through the patient and to the return electrode. In bipolar electrosurgery, both the active electrode and return electrode functions are performed at the site of surgery. Bipolar electrosurgical devices include two electrodes that are located in proximity to one another for the application of current between their surfaces. Bipolar electrosurgical current travels from one electrode, through the intervening tissue to the other electrode to complete the electrical circuit. Bipolar instruments generally include end-effectors, such as grippers, cutters, forceps, dissectors and the like. Electrosurgical generators are employed by surgeons in conjunction with a variety of types of monopolar and bipolar electrosurgical instruments to perform various types of electrosurgery.

Systems for performing an electrosurgical procedure may include a monopolar or bipolar electrosurgical instrument in operative communication with a processor for controlling the delivery of electrosurgical energy from the electrosurgical generator to the surgical instrument during the electrosurgical procedure. The processor may regulate the generator to adjust various parameters of the electrosurgical energy delivered to the patient during the electrosurgical procedure. Parameters of the delivered electrosurgical energy that may be regulated include voltage, current, resistance, intensity, power, frequency, amplitude, and/or waveform parameters.

An electrosurgical generator for supplying electrosurgical energy to tissue may be capable of switching among a plurality of electrosurgical operational modes such as monopolar and bipolar cutting and coagulation. Application duration and characteristics of the electrosurgical energy delivered to the patient may depend on a variety of factors such as the type of surgical procedure to be performed, surgical instrument design, tissue characteristics of the patient, and the progress of the heat distribution within the tissue area that is to be destroyed and/or the surrounding tissue.

In a variety of medical applications a patient isolation barrier is required for patient protection from unwanted and potentially hazardous voltages or currents. Isolation, broadly defined, is the separation of one circuit, component, or system from undesired influences of other circuits, components, or systems. Medical imaging devices may transmit data from isolated patient circuits to image processing circuits. Conventional handpieces typically include a plurality of switches (e.g., to allow the surgeon to change the mode of operation and/or parameters of the delivered electrosurgical energy) and may transmit control signals corresponding to switch positions across an isolation barrier. Control signals may cross this barrier by a variety of means, including magnetic coupling, optical coupling, and capacitive coupling.

Electromagnetic isolation uses a transformer to couple a signal across an isolation barrier, e.g., air or some other form of non-conductive barrier, by generating an electromagnetic field proportional to the electrical signal. The electromagnetic field may be created and detected by a pair of conductive coils. Optical coupling is the transmission of light across a transparent nonconductive barrier, typically an air gap, to achieve isolation. The light intensity is proportional to the measured signal. The light signal is transmitted across the isolation barrier and detected by a photoconductive element on the opposite side of the isolation barrier. Capacitive isolation is based on an electric field that changes with the level of charge on a capacitor plate. This charge is detected across an isolation barrier and is proportional to the level of the measured signal.

A need exists for reliable isolating devices suitable for use to transmit control signals from a handpiece to an electrosurgical power generator.

SUMMARY

A continuing need exists for methods and systems for transmitting data across a patient isolation barrier.

According to an aspect, an electric-field capacitive coupler module is provided. The electric-field capacitive coupler module includes a first processing unit, a first communication interface coupled to the first processing unit, a second communication interface, and an electric-field capacitive coupler apparatus that defines an isolation barrier. The electric-field capacitive coupler apparatus is coupled between the first communication interface and the second communication interface.

According to another aspect, system for transmitting data across a patient isolation barrier is provided. The system includes a handpiece including a surgical instrument, a control assembly coupled to the handpiece, and an electric-field capacitive coupler module. The electric-field capacitive coupler module includes a first processing unit, a first communication interface coupled to the first processing unit, a second communication interface, and an electric-field capacitive coupler apparatus that defines an isolation barrier. The electric-field capacitive coupler apparatus is coupled between the first communication interface and the second communication interface.

According to another aspect, a method of transmitting data across a patient isolation barrier is provided. The method includes the initial steps of receiving one or more analog electrical signals indicative of user input, and converting the one or more analog electrical signals into one or more digital signals. The method also includes the steps of transmitting the one or more digital signals through an electric-field capacitive coupler to a processing unit, and controlling an electrosurgical generator communicatively coupled to the processing unit based on the one or more digital signals.

BRIEF DESCRIPTION OF THE DRAWINGS

Objects and features of the presently-disclosed electric-field capacitive coupler modules, electrosurgical systems including the same, and methods of transmitting data across a patient isolation barrier will become apparent to those of ordinary skill in the art when descriptions of various embodiments thereof are read with reference to the accompanying drawings, of which.

DETAILED DESCRIPTION

Hereinafter, embodiments of the presently-disclosed electric-field capacitive coupler module and electrosurgical system including the same, and embodiments of the presently-disclosed method of transmitting data across a patient isolation barrier are described with reference to the accompanying drawings. Like reference numerals may refer to similar or identical elements throughout the description of the figures. As shown in the drawings and as used in this description, and as is traditional when referring to relative positioning on an object, the term "proximal" refers to that portion of the device, or component thereof, closer to the user and the term "distal" refers to that portion of the device, or component thereof, farther from the user.

This description may use the phrases "in an embodiment," "in embodiments," "in some embodiments," or "in other embodiments," which may each refer to one or more of the same or different embodiments in accordance with the present disclosure.

Electromagnetic energy is generally classified by increasing energy or decreasing wavelength into radio waves, microwaves, infrared, visible light, ultraviolet, X-rays and gamma-rays. As it is used in this description, "microwave" generally refers to electromagnetic waves in the frequency range of 300 megahertz (MHz) ($3 \times 10^8$ cycles/second) to 300 gigahertz (GHz) ($3 \times 10^{11}$ cycles/second). As it is used in this description, "ablation procedure" generally refers to any ablation procedure, such as microwave ablation, radio frequency (RF) ablation or microwave ablation assisted resection. As it is used in this description, "energy applicator" generally refers to any device that can be used to transfer energy from a power generating source, such as a microwave or RF electrosurgical generator, to tissue. As it is used in this description, "active electrode" generally refers to an electrode of an electrosurgical device that is adapted for producing an electrically-induced tissue treatment when brought into contact with, or close proximity to, a tissue targeted for treatment.

As it is used in this description, "printed circuit board" (or "PCB") generally refers to any and all systems that provide, among other things, mechanical support to electrical components, electrical connection to and between these electrical components, combinations thereof, and the like. The PCBs described herein may be manufactured from a wide range of materials including, without limitation, FR4 (flame retardant 4) PCB material, and low-loss dielectric PCB material, such as Rogers 4350, GETEK, or ARLON.

As it is used in this description, "transmission line" generally refers to any transmission medium that can be used for the propagation of signals from one point to another. As it is used in this description, "switch" or "switches" generally refers to any electrical actuators, mechanical actuators, electro-mechanical actuators (rotatable actuators, pivotable actuators, toggle-like actuators, buttons, etc.), optical actuators, or any suitable device that generally fulfills the purpose of connecting and disconnecting electronic devices, or component thereof, instruments, equipment, transmission line or connections and appurtenances thereto, or software.

As it is used herein, "electrical circuit" or simply "circuit" generally refers to a combination of a number of electrical devices and conductors that when connected together, form a conducting path to fulfill a desired function. Any constituent part of an electrical circuit other than the interconnections may be referred to as a "circuit element."

As it is used in this description, "user interface" generally refers to any visual, graphical, tactile, audible, sensory or other mechanism for providing information to and/or receiving information from a user or other entity. The term "user interface" as used herein may refer to an interface between a human user (or operator) and one or more devices to enable communication between the user and the device(s). Examples of user interfaces that may be employed in various embodiments of the present disclosure include without limitation, switches, potentiometers, buttons, dials, sliders, a mouse, keyboard, keypad, joysticks, trackballs, display screens, various types of graphical user interfaces (GUIs), touch screens, microphones and other types of sensors or devices that may receive some form of human-generated stimulus and generate a signal in response thereto.

Various embodiments of the present disclosure provide an electric-field capacitive coupler module. Various embodiments of the present disclosure provide electrosurgical systems and instruments suitable for sealing, cauterizing, coagulating/desiccating and/or cutting vessels and vascular tissue, ablating tissue, or otherwise modifying a tissue or organ of a patient, wherein the presently-disclosed electric-field capacitive coupler module provides a patient isolation barrier. In accordance with embodiments of the present disclosure, signals indicative of user input for controlling one or more operating parameters of an electrosurgical power generating source and/or at least some of the information monitored by various sensors, e.g., radiation detector and/or fluid-flow monitoring system, operably associated with the handpiece of a medical device may be transmitted across an electric-field capacitive coupler of the presently-disclosed electric-field capacitive coupler module.

Although the following description describes the use of electrosurgical systems including a handpiece with an energy applicator adapted for percutaneous energy delivery, the devices disclosed herein may be used with, or incorporated into, any suitable type of handheld medical device or electrosurgical energy delivery device including a handpiece having a surgical instrument, such as, for example, an open device, a catheter-type device, an endoscopic device, and a direct-contact, surface-delivery device.

Although the following description describes the use of an electrosurgical power generating source configured to operate in a coagulation or a cutting mode, the teachings of the present disclosure may also apply to a electrosurgical power generating source or generator assembly configured to operate in a variety of modes, such as ablation, monopolar and bipolar cutting, coagulation, and other modes.

Figures 1, 2:
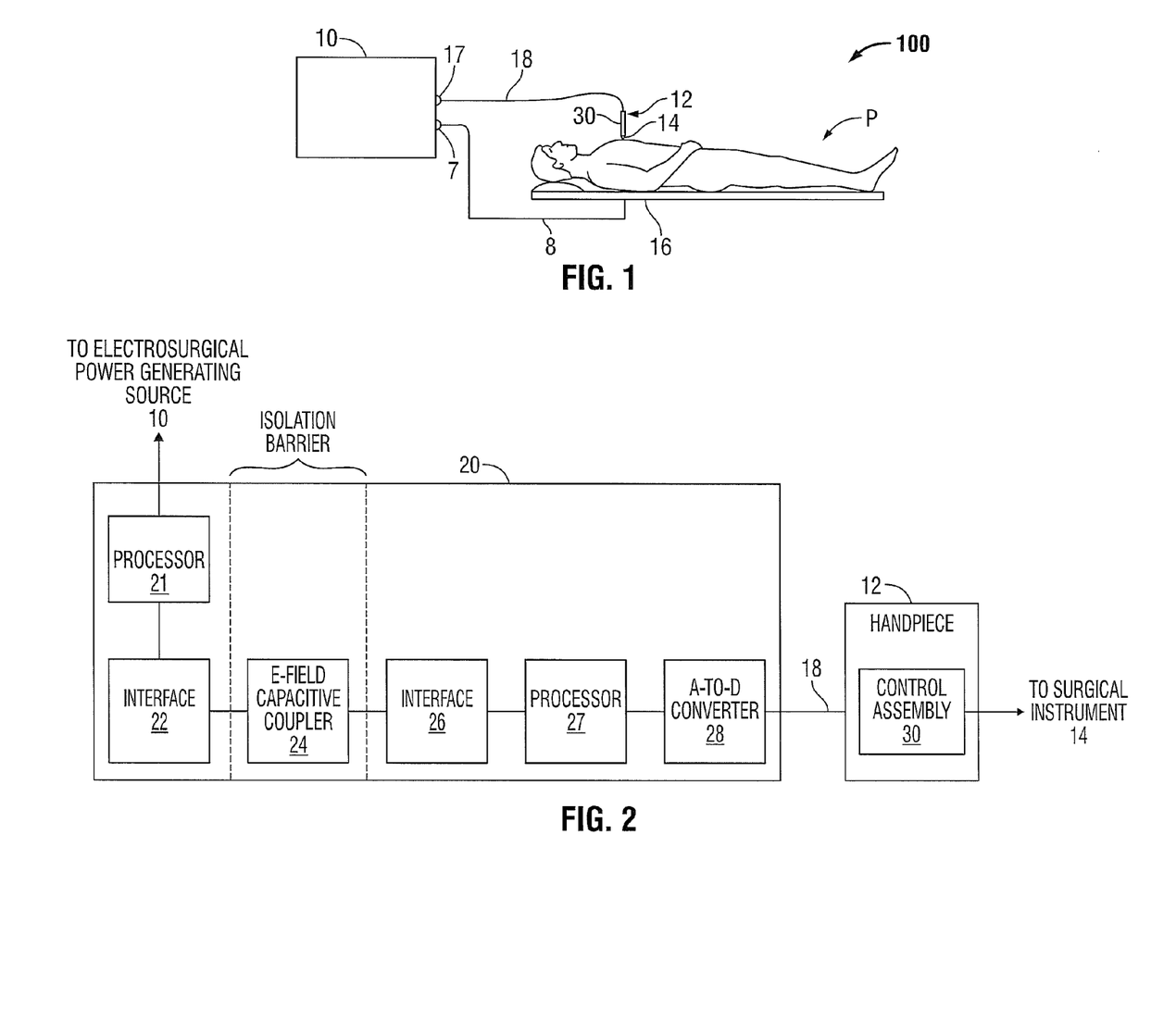
FIG. 1 is a schematic view of an electrosurgical system according to an embodiment of the present disclosure.
FIG. 2 is a block diagram of a handpiece and an electric-field capacitive coupler module according to an embodiment of the present disclosure.

FIG. 1 schematically illustrates an electrosurgical system 100 configured to selectively apply electrosurgical energy to target tissue of a patient P. Electrosurgical system 100 generally includes a handpiece 12 coupled via a transmission line 18 to an electrosurgical power generating source or generator assembly 10. Handpiece 12 includes a control assembly 30 and a surgical instrument 14. Generator assembly 10 may be any generator suitable for use with electrosurgical devices, and may be configured to provide various frequencies of energy. An embodiment of a generator assembly, such as the generator assembly 10 of FIG. 1, in accordance with the present disclosure, is shown in more detail in FIG. 3. It will be understood, however, that other generator assembly embodiments (e.g., microwave generator assembly 486 shown in FIG. 4 or generator assembly 50 shown in FIG. 5) may also be used.

Control assembly 30 generally includes a switch assembly 33 (shown in FIG. 3) which may include a plurality of switches. In some embodiments, the control assembly 30 may include one or more variable resistors. Examples of switch assembly embodiments are described in commonly-assigned U.S. patent application Ser. No. 11/338,479 filed on Jan. 24, 2006, entitled "METHOD AND SYSTEM FOR TRANSMITTING DATA ACROSS PATIENT ISOLATION BARRIER," the disclosure of which is herein incorporated by reference in its entirety. Control assembly 30 may include a variety of mechanisms adapted to generate signals for adjusting and/or controlling one or more operating parameters (e.g., temperature, impedance, power, current, voltage, mode of operation, and/or duration of application of electromagnetic energy) of the generator assembly 10.

Control assembly 30 may include an intensity controller adapted to allow the user to adjust the power parameters (e.g., voltage, power and/or current intensity) delivered to the surgical instrument 14. Intensity settings may be preset and selected from a look-up table, e.g., based on a choice of electrosurgical instruments and/or attachments, desired surgical effect, surgical specialty and/or surgeon preference. The selection may be made automatically or selected manually by the user. The intensity values may be predetermined or adjusted by the user. A variety of intensity controller designs and different locations of the intensity controller on the handpiece 12 may suitably be used. Examples of intensity controller embodiments are disclosed in commonly assigned U.S. Pat. No. 7,156,844, entitled "ELECTROSURGICAL PENCIL WITH IMPROVED CONTROLS", the disclosure of which is incorporated herein by reference in its entirety.

Surgical instrument 14 may include one or more energy applicators, e.g., one or more electrodes, or one or more antennas of any suitable type, such as an antenna assembly (or antenna array) suitable for use in tissue ablation applications. For ease of explanation and understanding, the surgical instrument 14 is described as including a single active electrode that is brought into contact with the patient P to effect a surgical procedure, e.g., cutting or coagulation, depending upon the operating mode selected.

The operating mode of the generator assembly 10 may depend on the setting of one or more switches of the switch assembly 33 associated with the handpiece 12. Handpiece 12 may include one or more electrically-conductive elements configured to permit electrical connection of the surgical instrument 14 to a connector (not shown), e.g., disposed at the proximal end of the handpiece 12. Handpiece 12 may be adapted to provide various configurations of electrical connections, e.g., one or more electric conductors suitably adapted for transfer of communication signals and/or electric power.

Handpiece 12 and the transmission line 18 may have various dimensions, e.g., diameter and length. Transmission line 18 may be cooled by fluid, e.g., saline or water, to improve power handling. Handpiece 12 may be provided with a coolant chamber (not shown). Handpiece 12 may include one or more sensors for sensing a condition and producing a signal indicative of the sensed condition. Handpiece 12 may utilize resistive element networks, e.g., instead of relying on switch activation signals, to provide for greater range of control selection with fewer wires.

Transmission line 18 may be formed from a suitable flexible, semi-rigid or rigid cable, and may connect directly to the generator assembly 10. In some embodiments, the transmission line 18 electrically connects the surgical instrument 14 to an output 17 of the generator assembly 10. Transmission line 18 may be internally divided into a plurality of cable leads or wires, each of which transmits electrosurgical energy and/or communication signals through their respective feed paths to the surgical instrument 14 and/or to the generator assembly 10. One of the wires conducts electrosurgical current from the generator assembly 10 to the active electrode, hereafter referred to as the active line. In some embodiments, the active line also conducts DC voltage from the generator assembly 10 which is employed by the handpiece 12 to transmit input signals back thereto. A DC voltage source may be used to transmit a control current which is used by the handpiece 12 to transmit input signals to the generator assembly 10. Transmission line 18 may additionally, or alternatively, provide a conduit (not shown) configured to provide coolant fluid from a coolant source (not shown) to one or more components of the handpiece 12 and/or surgical instrument 14.

In some embodiments, a return electrode 16 is attached externally to the patient P and returns the electrosurgical current from the patient P to the generator assembly 10. Return electrode 16 may be coupled to a transmission line 8 that electrically connects the return electrode 16 to an input 7 of the generator assembly 10.

FIG. 2 schematically illustrates an electric-field capacitive coupler module 20 according to an embodiment of the present disclosure that is operably coupled to the handpiece 12. Electric-field capacitive coupler module 20 generally includes a first processing unit 27, a first communication interface 26 coupled to the first processing unit 27, and an electric-field capacitive coupler 24 that defines an isolation barrier coupled between the first communication interface 26 and a second communication interface 22. Electric-field capacitive coupler module 20 may be configured to provide various configurations of electrical connections between one or more components thereof and a power source, e.g., generator assembly 10 of FIG. 1. In some embodiments, the electric-field capacitive coupler module 20 may be configured as a stand-alone device, and may include a self-contained power source (not shown).

Electric-field capacitive coupler module 20 is configured to transmit data across the isolation barrier defined by the electric-field capacitive coupler 24. Any data stream may be transmitted by the electric-field capacitive coupler 20. In some embodiments, the data may be directly transmitted across the electric-field capacitive coupler 20. Data transmitted by the electric-field capacitive coupler module 20 may additionally, or alternatively, be modulated using pulse position modulation (PPM), pulse width modulation (PWM), phase reversal modulation, frequency modulation (FM), or any other modulation techniques. In some embodiments, the data may be modulated onto a higher frequency carrier. Methods of data transfer with high rates of transition may exhibit improved performance using the presently-disclosed electric-field capacitive coupler module 20, e.g., due to the non-ideal leakage characteristics of the receiver.

Figure 6:
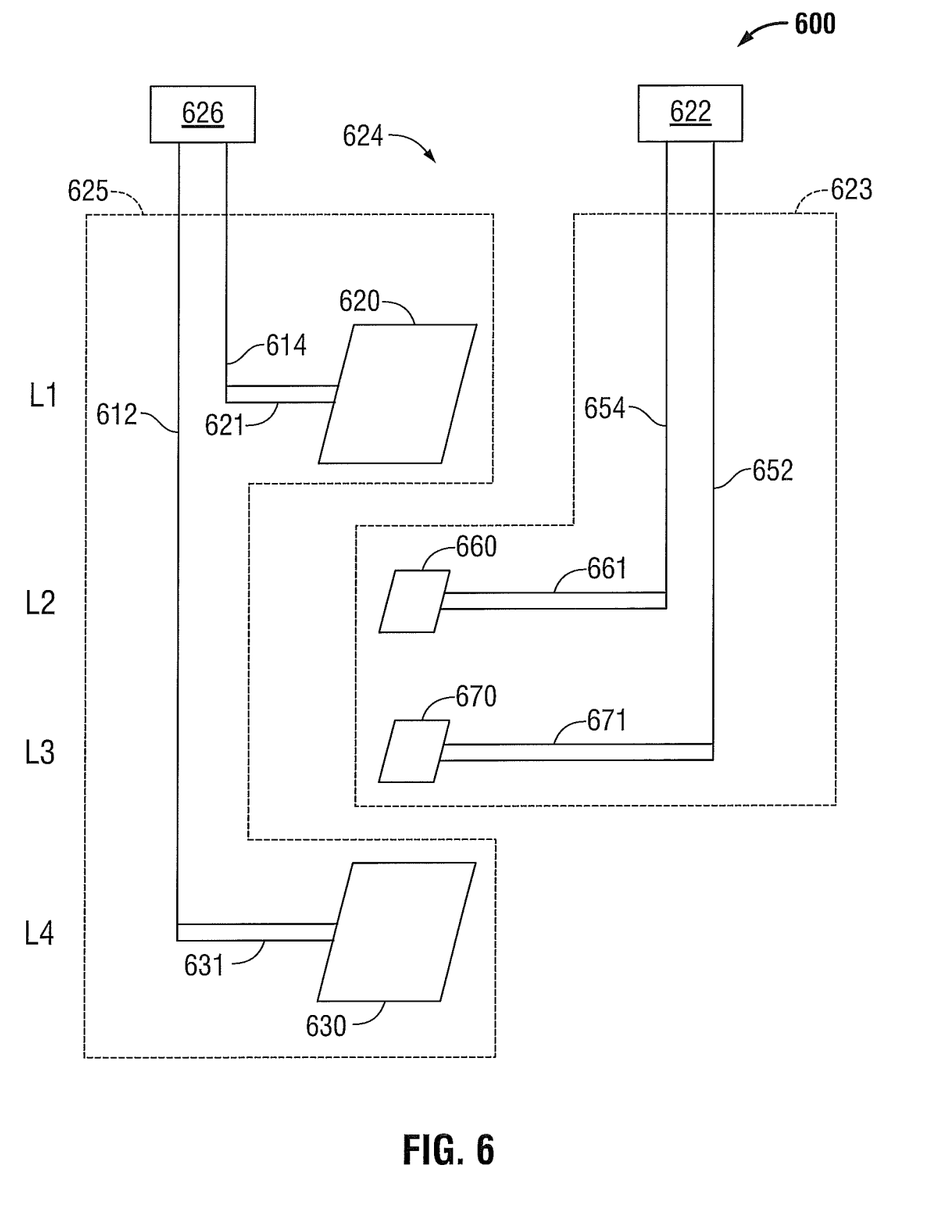
FIG. 6 is a schematic view of a portion of a multi-layer printed circuit board including an electric-field capacitive coupler, such as the electric-field capacitive coupler shown in FIG. 2, according to an embodiment of the present disclosure.

Electric-field capacitive coupler 24 generally includes a configuration of electrically-conductive plates for providing an isolation device. Electric-field capacitive coupler 24, or portions thereof, may be embedded and/or attached to a printed circuit board. An embodiment of an embedded configuration of the electric-field capacitive coupler 24 is schematically illustrated in FIG. 6. In alternative embodiments not shown, electric-field capacitive coupler 24 may be a purpose-built device. In some embodiments, as shown in FIG. 6, the electric-field capacitive coupler 24 is configured as a four-terminal device that includes two transmit plates (e.g., plates 620 and 630 shown in FIG. 6) and two receive plates (e.g., plates 660 and 670 shown in FIG. 6) disposed between the two transmit plates.

First communication interface 26 and/or the second communication interface 22 may be a bidirectional or unidirectional device, and may include one or more transmitters, receivers, and/or transceivers. First communication interface 26 and/or the second communication interface 22 may include one or more electric-field sensors, and may utilize a wide variety of electric-field sensing schemes, e.g., using electro-optic devices and/or other sensing devices (e.g., sensor devices either using electrodes or electrode-less). In some embodiments, optical techniques may be employed that use light to sense electric fields by taking advantage of their interaction in electro-optic crystals. In some embodiments, electric-fields may be sensed using coherence modulation of light. In electric-field sensing schemes based on the electro-optic interaction between light and electric fields, the electric field may modulate the intensity of an optical beam passing through an electro-optic bulk crystal or optical waveguide. Optical intensity modulators can be implemented by two-wave interferometers such as polarization or Mach-Zehnder. In some embodiments, the sensed electric field may modulate an optical delay, instead of the optical intensity, e.g., electric fields may be sensed by schemes associating low-coherence optical sources and one or more electro-optical polarization interferometers.

In some embodiments, as shown in FIG. 2, the electric-field capacitive coupler module 20 includes a second processing unit 21 communicatively coupled to the second communication interface 22. In alternative embodiments not shown, a single processing unit (e.g., first processing unit 27 shown in FIG. 2, or processing unit 82 shown in FIG. 3, or processing unit 582 shown in FIG. 5) may be communicatively coupled to each one of the first communication interface 26 and the second communication interface 22.

The first processing unit 27 may receive electrical signals from the A-to-D converter 28 and/or the control assembly 30. The control assembly may be configured to process the user input to provide one or more signals indicative of the user input and/or interpretation of the user input for adjusting and/or controlling one or more operating parameters (e.g., temperature, impedance, power, current, voltage, mode of operation, and/or duration of application of electromagnetic energy) of the generator assembly 10. The first processing unit 27 is adapted to format the data received from the A-to-D converter 28 and/or the control assembly 30 for transmission across the isolation barrier, as shown in FIG. 2, via the E-field capacitive coupler 24.

The second processing unit 21 receives the data from the E-field capacitive coupler 24. The second processing unit 21 may be configured to perform data processing and/or data conversion, e.g., the second processing unit 21 may convert and/or format the data for use by the generator assembly 10. In some embodiments, the second processing unit 21 may be configured to determine whether to send the raw data received from the E-field capacitive coupler 24 for processing by the generator assembly 10.

First processing unit 27 and/or the second processing unit 21 may include any type of computing device, computational circuit, or any type of processor or processing circuit capable of executing a series of instructions that are stored in a memory. The first and second processing units 27 and 21, respectively, may include multiple processors and/or multi-core CPUs and may include any type of processor, such as a microprocessor, digital signal processor, microcontroller, or the like.

In some embodiments, as shown in FIG. 2, the electric-field capacitive coupler module 20 includes an analog-to-digital (A-to-D) converter 28 coupled to the first processing unit 27. A-to-D converter 28 may receive an analog input signal, representing a signal from the control assembly 30 indicative of user input, or a signal from a sensor indicative of a sensed condition, or other electrical signal from the handpiece 12, and generates a digital output signal, which may be provided to the first processing unit 27.

In some embodiments, wherein the electrosurgical system 100 includes an A-to-D converter 28, the first processing unit 27 may be configured to control configuration of the A-to-D converter 28 and data conversions. This would allow the second processing unit 21 (and/or processor 82 shown in FIG. 3) to wait for input from the first processor 27 that indicates a change in user request, which, in turn, may result in lower system latency and lower main processor overhead.

In alternative embodiments not shown, the handpiece 12 may include a radiation detector. The radiation detector may include any suitable device capable of detecting electromagnetic radiation and converting it to another form of energy such as electrical signals, and may be coupled via the electric-field capacitive coupler module 20 to the generator assembly 10. Examples of radiation detector embodiments are disclosed in commonly assigned U.S. patent application Ser. No. 12/542,785 filed on Aug. 18, 2009, entitled "MICROWAVE ABLATION ANTENNA RADIATION DETECTOR", the disclosure of which is incorporated herein by reference in its entirety.

In alternative embodiments not shown, the handpiece 12 may include a fluid-flow monitoring system adapted to monitor and/or regulate the pressure and/or flow rate of fluid and capable of generating a signal indicative of an abnormal fluid circulation condition. The fluid-flow monitoring system may include one or more sensors disposed in fluid communication with the surgical instrument 14 capable of sensing the pressure and/or flow rate of fluid flow in and/or out of the surgical instrument 14. In such case, the sensors may be coupled via the electric-field capacitive coupler module 20 to the generator assembly 10. Examples of fluid-flow monitoring system embodiments are disclosed in commonly assigned U.S. patent application Ser. No. 12/568,972 filed on Sep. 29, 2009, entitled "FLOW RATE MONITOR FOR FLUID COOLED MICROWAVE ABLATION PROBE", U.S. patent application Ser. No. 12/566,299 filed on Sep. 24, 2009, entitled "OPTICAL DETECTION OF INTERRUPTED FLUID FLOW TO ABLATION PROBE", and U.S. patent application Ser. No. 12/569,685 filed on Sep. 29, 2009, entitled "FLOW RATE MONITOR FOR FLUID COOLED MICROWAVE ABLATION PROBE", the disclosures of which are incorporated herein by reference in their entireties.

Figure 3:
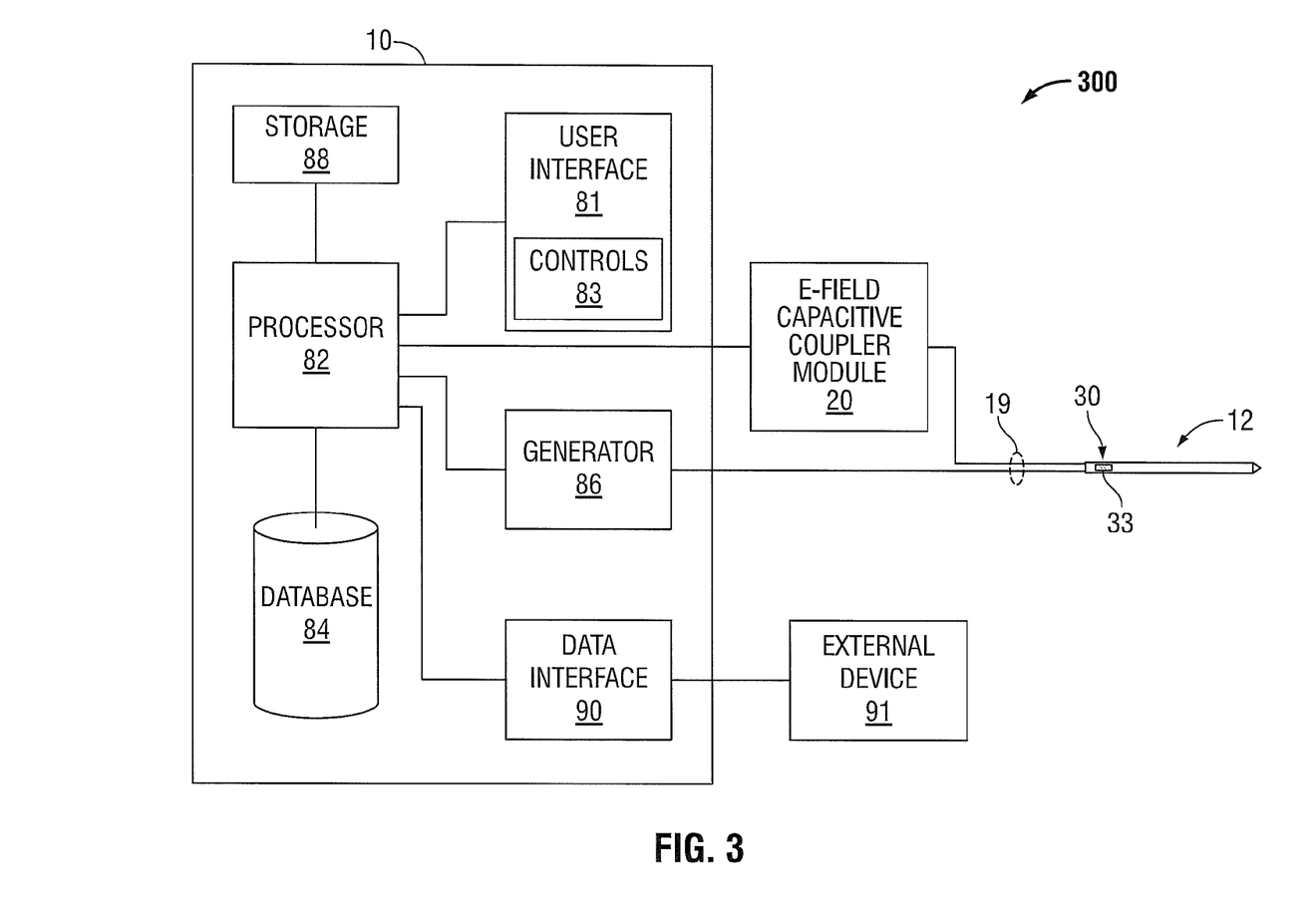
FIG. 3 is a block diagram of an electrosurgical system including a handpiece, an electrosurgical power generating source, and an electric-field capacitive coupler module, such as the electric-field capacitive coupler module shown in FIG. 2, according to an embodiment of the present disclosure.

FIG. 3 schematically illustrates an electrosurgical system (shown generally as 300) including an embodiment of the generator assembly 10 of FIG. 1 that includes a generator module 86 in operable communication with a processing unit 82. Generator module 86 may be configured to provide various frequencies of energy. In some embodiments, the generator module 86 may be configured to provide energy at an operational frequency from about 300 MHz to about 10 GHz. Handpiece 12 is operably coupled to the generator module 86. In some embodiments, as shown in FIG. 3, the electric-field capacitive coupler module 20 of FIG. 2 is coupled between the processing unit 82 and the handpiece 12. A suitable flexible, semi-rigid or rigid cable assembly 19 may be provided to electrically-couple the handpiece 12 to the electric-field capacitive coupler module 20 and/or the generator module 86.

Processing unit 82 may be communicatively coupled to a user interface 81. User interface 81 may include a display (not shown), such as without limitation a flat panel graphic LCD (liquid crystal display). User interface 81 may additionally, or alternatively, include one or more controls 83 that may include without limitation a switch (e.g., pushbutton switch, toggle switch, slide switch) and/or a continuous actuator (e.g., rotary or linear potentiometer, rotary or linear encoder). In some embodiments, one or more controls 83 may have a dedicated function, e.g., display contrast, power on/off, and the like. One or more controls 83 may have a function that may vary in accordance with an operational mode of the generator assembly 10.

In some embodiments, a storage device 88 is operably coupled to the processing unit 82, and may include random-access memory (RAM), read-only memory (ROM), and/or non-volatile memory (NV-RAM, Flash, and disc-based storage). Generator assembly 10 may include a data interface 90 that is configured to provide a communications link to an external device 91. In an embodiment, the data interface 90 may be any of a USB interface, a memory card slot (e.g., SD slot), and/or a network interface (e.g., 100BaseT Ethernet interface or an 802.11 "Wi-Fi" interface). External device 91 may be any of a USB device (e.g., a memory stick), a memory card (e.g., an SD card), and/or a network-connected device (e.g., computer or server).

Processing unit 82 may include any type of computing device, computational circuit, or any type of processor or processing circuit capable of executing a series of instructions that are stored in a memory, e.g., storage device 88 or external device 91. Generator assembly 10 may also include a database 84 communicatively coupled to the processing unit 82 and configured to store and retrieve data, e.g., parameters associated with one or energy applicators (e.g., surgical instrument 14). Database 84 may be maintained at least in part by data provided by the external device 91 via the data interface 90. For example without limitation, energy applicator data and/or other data may be uploaded from the external device 91 to the database 84 via the data interface 90.

Figure 4:
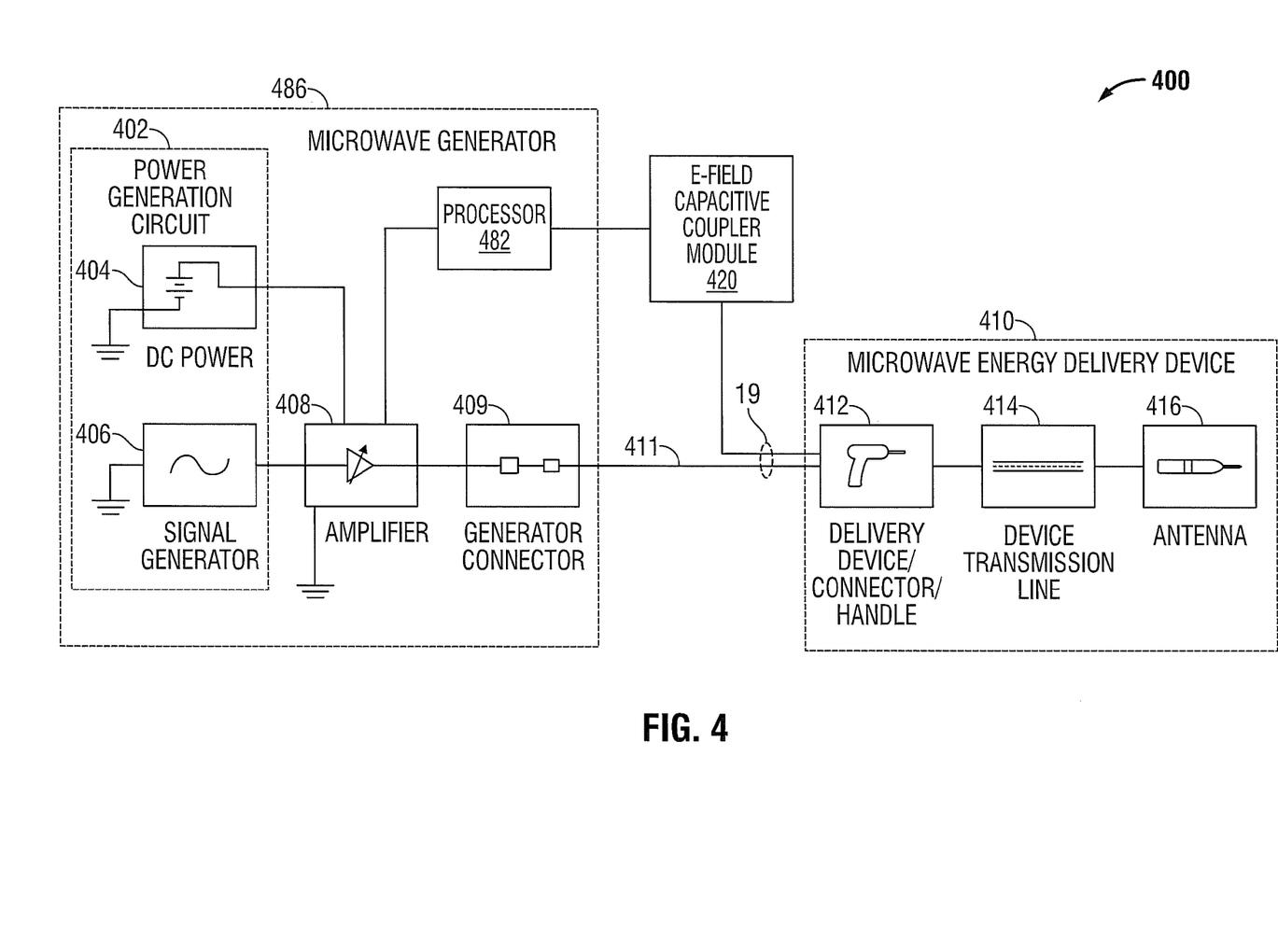
FIG. 4 is a block diagram of an electrosurgical system including an electric-field capacitive coupler module, such as the electric-field capacitive coupler module shown in FIG. 2, coupled between a microwave generator and a microwave energy delivery device according to an embodiment of the present disclosure.

FIG. 4 schematically illustrates an electrosurgical system (shown generally as 400) that includes an electric-field capacitive coupler module 420 coupled between a microwave generator assembly 486 and a microwave energy delivery device 410. Electric-field capacitive coupler module 420 may utilize different configurations of components, some with additional, fewer, or different components than the stand-alone electric-field capacitive coupler module 20 shown in FIG. 2, depending upon a particular purpose or to achieve a desired functionality. For example without limitation, electric-field capacitive coupler module 420 may utilize the processing unit 482 shown in FIG. 4 instead of either one or both of the first processing unit 27 and the second processing unit 21 of the electric-field capacitive coupler module 20 shown in FIG. 2.

Microwave generator assembly 486 includes a power generation circuit 402 that generates and provides DC power from a DC power supply 404 and a microwave frequency signal from a signal generator 406. Microwave generator assembly 486 includes an amplifier unit 408, and may include a processing unit 482 communicatively coupled to the amplifier unit 408 and configured to control the amplifier unit 408 to amplify the microwave frequency signal generated by the signal generator 406 to a desired power level. DC power from the DC power supply 404 and the microwave frequency signal from the signal generator 406 are supplied to the amplifier unit 408. Amplifier unit 408 may include one or more microwave signal amplifiers configured to amplify the microwave frequency signal, e.g., based on one or more signals received from the processing unit 482, from a first power level to at least one second power level. Processing unit 482 is similar to the processing unit 82 shown in FIG. 2, and further description thereof is omitted in the interests of brevity.

The microwave frequency signal outputted from the microwave amplifier unit 408 is supplied to a first end of the transmission line 411 connected to the generator connector 409. In some embodiments, the second end of the transmission line 411 connects to the delivery device connector 412 of the microwave energy delivery device 410. A suitable flexible, semi-rigid or rigid transmission line, e.g., cable assembly 19, may additionally, or alternatively, be provided to electrically-couple the microwave energy delivery device 410 to the electric-field capacitive coupler module 20 and/or the generator connector 409. The microwave frequency signal is passed through the device transmission line 414 to the antenna 416 at the distal end of the microwave energy delivery device 410.

Figure 5:
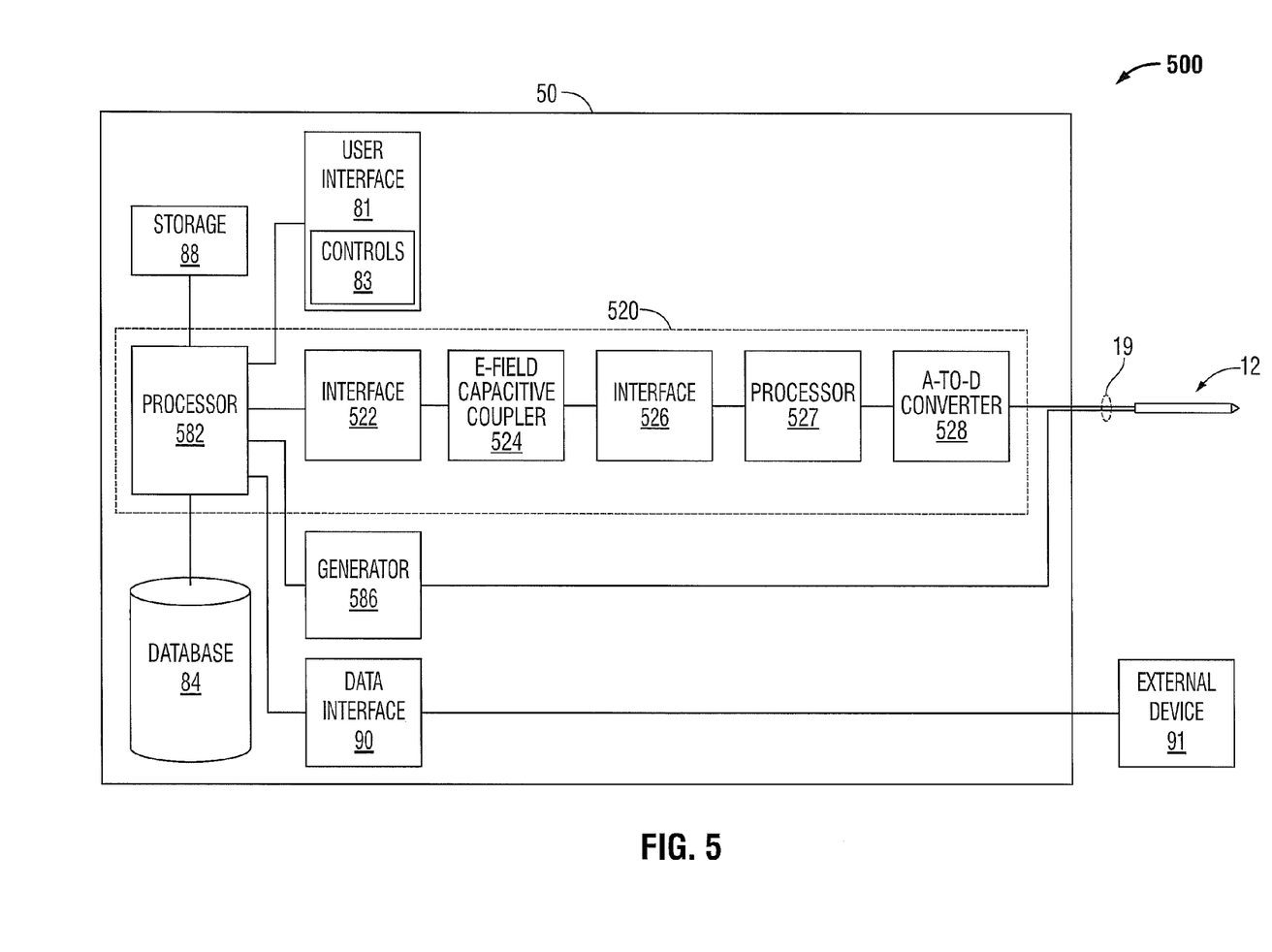
FIG. 5 is a block diagram of an electrosurgical system including a handpiece, such as the handpiece shown in FIG. 1, and an electrosurgical power generating source according to an embodiment of the present disclosure.

FIG. 5 schematically illustrates an electrosurgical system (shown generally as 500) including a generator assembly 50 according to an embodiment of the present disclosure that includes an electric-field capacitive coupler module 520 operably coupled to the handpiece 12. Generator assembly 50 includes a generator module 586 in operable communication with a processing unit 582. In some embodiments, the generator assembly 50 may include the user interface 81 shown in FIG. 3 operably coupled to the processing unit 582. Generator assembly 50 may additionally, or alternatively, include the database 84, the data interface 90 and/or the storage device 88 shown in FIG. 3.

Electric-field capacitive coupler module 520 is operably coupled to the handpiece 12, and generally includes a first communication interface 526 coupled to the processing unit 582, a second communication interface 522, and an electric-field capacitive coupler 524 coupled between the first and second communication interfaces 526 and 522, respectively. First communication interface 526, the electric-field capacitive coupler 524, and the second communication interface 522 shown in FIG. 5 are similar to the first communication interface 26, the electric-field capacitive coupler 24, and the second communication interface 22, respectively, shown in FIG. 2, and further description thereof is omitted in the interests of brevity. In some embodiments, as shown in FIG. 5, the electric-field capacitive coupler module 520 includes a processing unit 527 coupled between the second communication interface 526 and an analog-to-digital (A-to-D) converter 528. Processing unit 527 and the A-to-D converter 582 shown in FIG. 5 are similar to the first processing unit 27 and the A-to-D converter 28, respectively, shown in FIG. 2, and further description thereof is omitted in the interests of brevity.

FIG. 6 schematically illustrates a portion of a multi-layer printed circuit board (shown generally as 600) including an embedded configuration of an electric-field capacitive coupler 624 according to an embodiment of the present disclosure that includes a first portion 623 electrically-coupled to a receiver 622 and a second portion 625 electrically-coupled to a driver 626. In alternative embodiments not shown, the electric-field capacitive coupler 624 may be a standalone apparatus, and may be electrically coupled to one or more traces and/or components of a printed circuit board.

Printed circuit board (PCB) 600 generally includes one or more layer stacks formed of a plurality of layers of suitable electrically-conductive and/or non-conductive materials. Examples of suitable materials may include, without limitation, dielectrics, e.g., polytetrafluoroethylene (Teflon®), FR-4 (flame retardant 4), CEM-1 or CEM-3, low-loss dielectric PCB material, e.g., Rogers 4350, GETEK® or ARLON, electrically-conductive materials such as without limitation metal, e.g., copper foil, fibrous materials, e.g., carbon, graphite, graphene, glass, quartz, polyethylene or liquid crystal polymer fibers, prepreg materials, e.g., FR-2 (phenolic cotton paper), FR-3 (cotton paper and epoxy), FR-4 (woven glass and epoxy), FR-5 (woven glass and epoxy), FR-6 (matte glass and polyester), G-10 (woven glass and epoxy), CEM-1 (cotton paper and epoxy), CEM-2 (cotton paper and epoxy), CEM-3 (woven glass and epoxy), CEM-4 (woven glass and epoxy) or CEM-5 (woven glass and polyester), or other suitable electrically-conductive or non-conductive materials, e.g., fibrous materials with low coefficients of thermal expansion that are metalized to provide a resultant electrically-conductive material with a low coefficient of thermal expansion.

In addition to patterns of electrically-conductive traces on one or more layers of the multi-layer PCB 600, a patterned array of metal-filled through-holes, or vias, may be formed to allow for layer-to-layer interconnections between various conductive features. PCB 600 may utilize different configurations of layer stacks and electrically-conductive pathways, some with additional layers and/or fewer, additional or different electrically-conductive pathways than the PCB 600 shown in FIG. 6.

First portion 623 includes a first electrically-conductive plate 660 disposed on the second layer L2 of the printed circuit board (PCB) 600 and a second electrically-conductive plate 670 disposed on the third layer L3 of the PCB 600. Second portion 625 includes a third electrically-conductive plate 620 disposed on the first layer L1 of the PCB 600 and a fourth electrically-conductive plate 630 disposed on the fourth layer L4 of the PCB 600. First, second, third and fourth electrically-conductive plates 660, 670, 620 and 630, respectively, may be formed of any suitable electrically-conductive material, e.g., metal, and may have any suitable shape, e.g., square, circular or rectangular.

First electrically-conductive plate 660 is coupled to a first electrically-conductive trace 661 (e.g., strip-line trace) which, in turn, is coupled via a first electrically-conductive pathway 654 to the receiver 622. Second electrically-conductive plate 670 is coupled to a second electrically-conductive trace 671 (e.g., strip-line trace) which, in turn, is coupled via a second electrically-conductive pathway 652 to the receiver 622. In some embodiments, the first electrically-conductive pathway 654 and/or the second electrically-conductive pathway 652 may include one or more electrically-conductive vias. The voltage on the first and second electrically-conductive plates 660 and 670, respectively, may be amplified by the receiver 622. In some embodiments, the receiver 622 may be a differential receiver.

Third electrically-conductive plate 620 is coupled to a third electrically-conductive trace 621 (e.g., strip-line trace) which, in turn, is coupled via a third electrically-conductive pathway 614 to the driver 626. Fourth electrically-conductive plate 630 is coupled to a fourth electrically-conductive trace 631 (e.g., strip-line trace) which, in turn, is coupled via a fourth electrically-conductive pathway 612 to the driver 626. In some embodiments, the third electrically-conductive pathway 614 and/or the fourth electrically-conductive pathway 612 may include one or more electrically-conductive vias. Third and fourth electrically-conductive plates 620 and 630, respectively, are driven by the driver 626. This generates an electric field between the third and fourth electrically-conductive plates 620 and 630, respectively. The electric field is coupled to the first and second electrically-conductive plates 660 and 670, respectively, and impresses a voltage thereon. In some embodiments, the driver 626 may be a single-ended transmitter or a differential transmitter.

In alternative embodiments not shown, the third electrically-conductive plate 620 and the fourth electrically-conductive plate 630 may be disposed on layers other than the first and fourth layers, respectively, of a multi-layer PCB, and the first electrically-conductive plate 660 and the second electrically-conductive plate 670 may be disposed on layers other than the second and third layers, respectively. Various configurations of multi-layer PCBs may include the presently-disclosed electric-field capacitive coupler 624, wherein the first and second electrically-conductive plates 660 and 670 are disposed on layers in the stack-up disposed outwardly of the third and fourth electrically-conductive plates 620 and 630, which, in turn, are disposed on layers in the stack-up disposed inwardly of the first and second electrically-conductive plates 660 and 670.

As an illustrative and non-limiting example, the first and second electrically-conductive plates 660 and 670 may be disposed on the first and eighth layers, respectively, of a PCB, and the third and fourth electrically-conductive plates 620 and 630 may be disposed on the fourth and fifth layers, respectively. It is to be understood that any stack-up of layers that provides isolation between the first and second electrically-conductive plates 660 and 670 and the third and fourth electrically-conductive plates 620 and 630 may be utilized.

Figure 7:
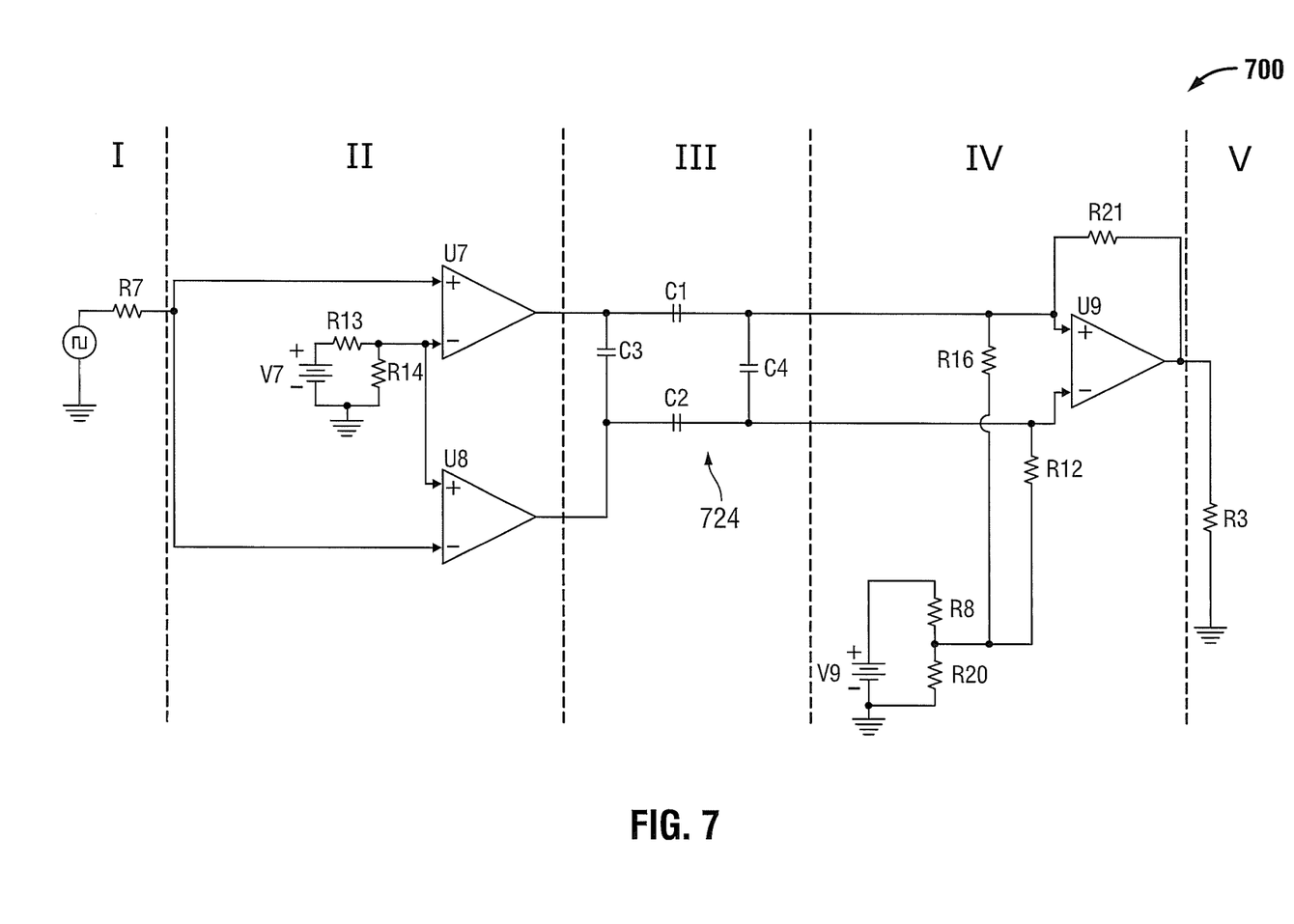
FIG. 7 is a schematic view of a circuit including an electric-field capacitive coupler model according to an embodiment of the present disclosure.

FIG. 7 schematically illustrates a circuit (shown generally as 700) that includes an embodiment of an electric-field capacitive coupler model 724. For ease of explanation and understanding, the circuit 700 is divided by vertical dashed lines into a plurality of regions I, II, III, IV and V, e.g., representing schematically electrical models of circuit components.

The first region I of the circuit 700 represents an electrical model of the first processing unit 27 or the second processing unit 21, depending on the direction of data flow.

The second region II of the circuit 700 represents an electrical model of the first communication interface 26 or the second communication interface 22 of FIG. 2 (or first communication interface 526 or second communication interface 522 of FIG. 5), depending on the direction of data flow.

Electric-field capacitive coupler module 724 is shown in the third region III of the circuit 700 and includes four capacitors C1, C2, C3 and C4.

The fourth region IV of the circuit 700 represents an electrical model of the first communication interface 26 or the second communication interface 22 of FIG. 2 (or first communication interface 526 or second communication interface 522 of FIG. 5), depending on the direction of data flow.

The fifth region V of the circuit 700 represents an electrical model of the first processing unit 27 or the second processing unit 21, depending on the direction of data flow.

The presently-disclosed electric-field capacitive coupler may be configured to allow bidirectional data flow in a single device. In some embodiments, the layering of the plates can be altered by changing the connection data flow from the second electrically-conductive plate 670 to the fourth electrically-conductive trace 631 and from the fourth electrically-conductive plate 630 to the second electrically-conductive trace 671.

Hereinafter, methods of transmitting data across a patient isolation barrier are described with reference to FIGS. 8 and 9. It is to be understood that the steps of the methods provided herein may be performed in combination and in a different order than presented herein without departing from the scope of the disclosure.

Figure 8:
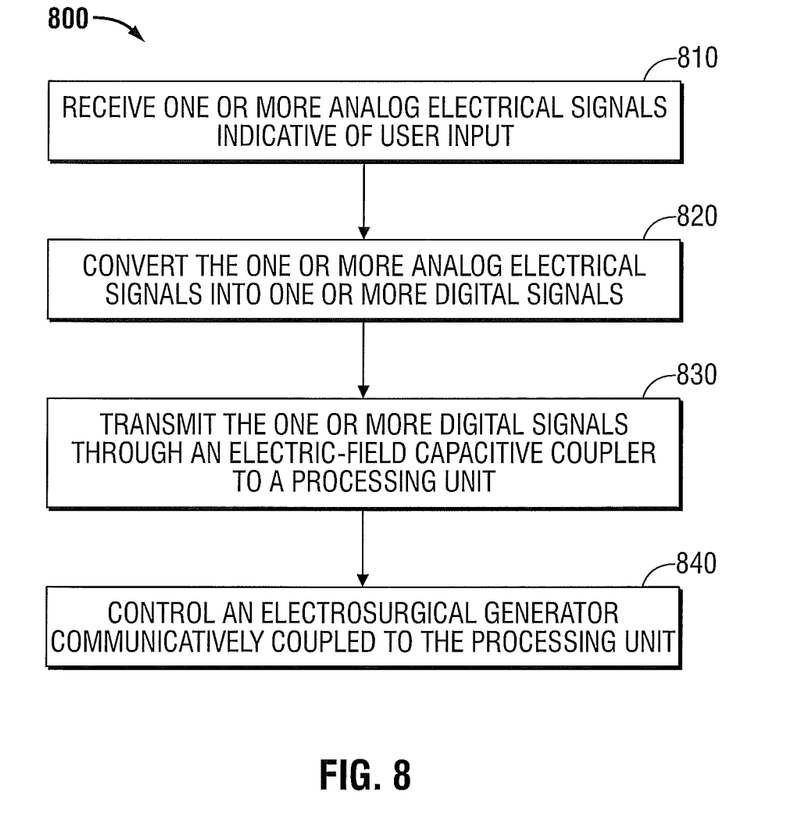
FIG. 8 is a flowchart illustrating a method of controlling an electrosurgical generator through a patient isolation barrier according to an embodiment of the present disclosure.

FIG. 8 is a flowchart illustrating a method of transmitting data across a patient isolation barrier according to an embodiment of the present disclosure. In step 810, one or more analog electrical signals indicative of user input are received. The analog electrical signal(s) may correspond to the input(s) at a control assembly 30 associated with a handpiece 12.

In step 820, the one or more analog electrical signals are converted into one or more digital signals. In some embodiments, an A-to-D converter 28 receives an analog input signal, representing a signal from the control assembly 30 indicative of user input, or a signal from a sensor indicative of a sensed condition, or other electrical signal from the handpiece 12, and generates a digital output signal.

In step 830, the one or more digital signals are transmitted through an electric-field capacitive coupler 24 to a processing unit 21. In some embodiments, transmitting the one or more digital signals through an electric-field capacitive coupler 24 to a processing unit 21, in step 830, may include the steps of: transmitting the one or more digital signals to a first communication interface 26; transmitting the one or more digital signals from the first communication interface 26 through the electric-field capacitive coupler 24 to a second communication interface 22; and transmitting the one or more digital signals from the second communication interface 26 to the processing unit 21.

In step 840, an electrosurgical generator 10 communicatively coupled to the processing unit 21 is controlled based on the one or more digital signals.

Figure 9:
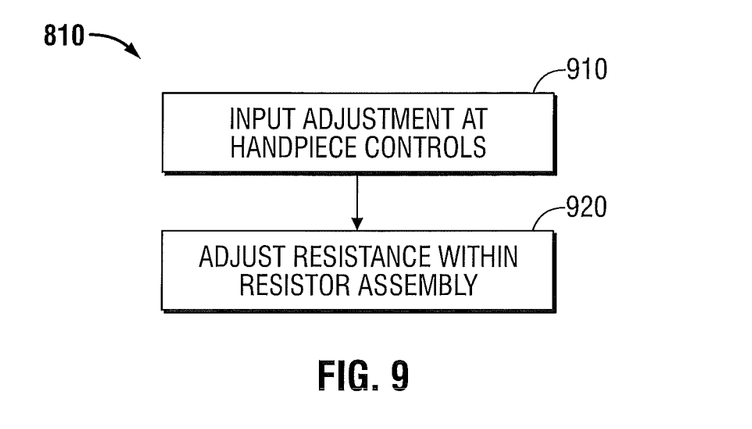
FIG. 9 is a flowchart illustrating an embodiment of the step of receiving one or more electrical signals indicative of user input of the method illustrated in FIG. 8 according to the present disclosure.

As illustrated in FIG. 9, the step 810 shown in FIG. 8 may further include steps 910 and 920. In step 910, the surgeon inputs adjustments into the control assembly 30 (e.g., increasing the intensity by 10%) by pressing buttons and/or activating switches 33, potentiometers and/or other types of sensors or devices that may receive some form of human-generated stimulus and generate a signal in response thereto.

In step 920, the pressing of buttons activates corresponding switches 33 which, in turn, modifies the resistance within a resistor assembly (not shown). The resistance adjusts the DC voltage passing through the resistor assembly which corresponds to inputs at the control assembly 30.

Figure 10:
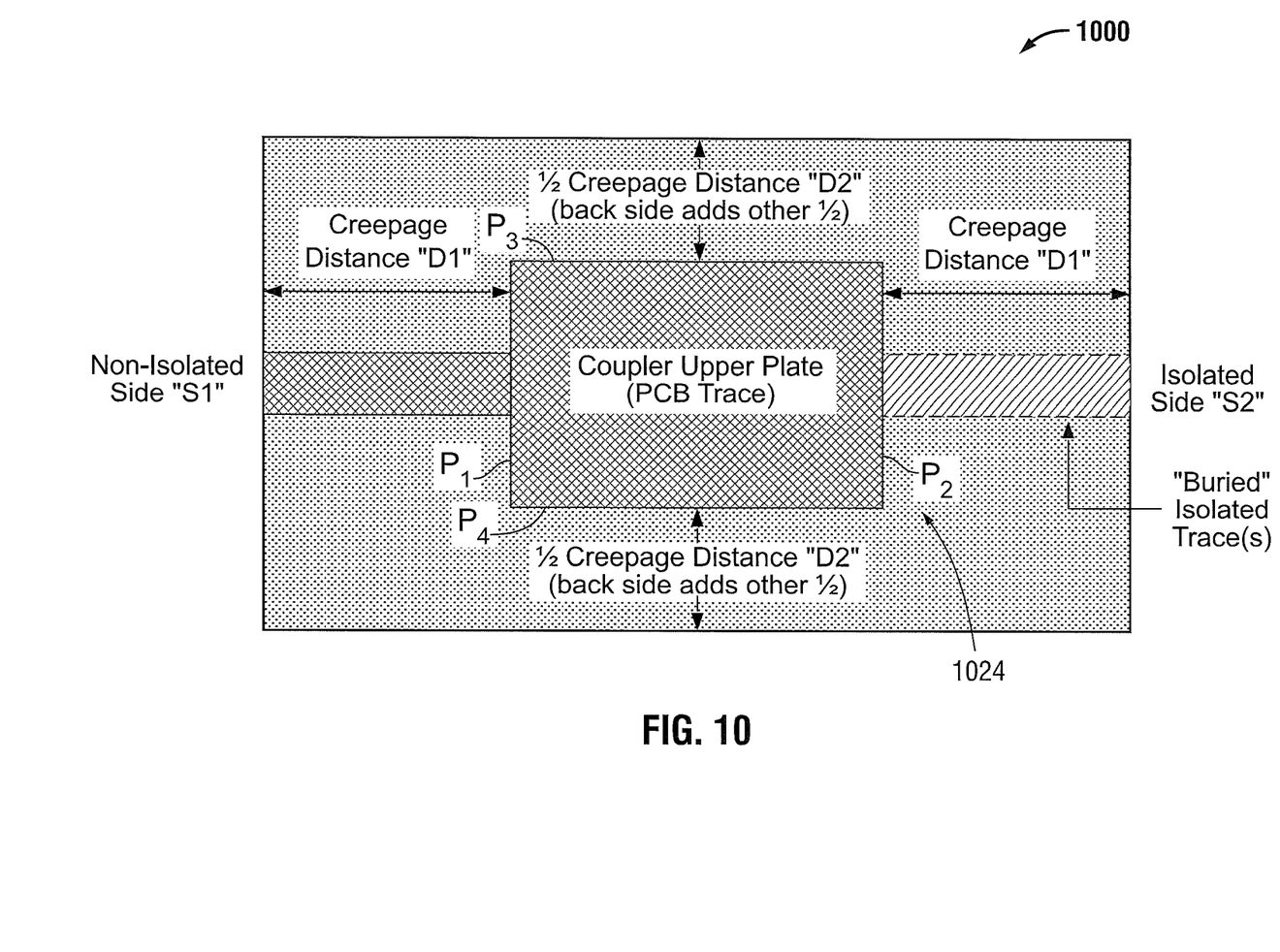
FIG. 10 is an enlarged top view of a portion of a printed circuit board including an electric-field capacitive coupler according to an embodiment of the present disclosure.

FIG. 10 shows a portion of a printed circuit board (shown generally as 1000) that includes an electric-field capacitive coupler 1024 according to an embodiment of the present disclosure. Electric-field capacitive coupler 1024 includes a non-electrically isolated side "S1", an electrically-isolated side "S2", and a coupler upper plate. In some embodiments, as shown in FIG. 10, the coupler upper plate has a substantially rectangular shape including a first side $P_1$, a second side $P_2$, a third side $P_3$, and a fourth side $P_4$.

In some embodiments, a creepage distance "D1" is provided between the first side $P_1$ of the coupler upper plate and the locations of elements (not shown) disposed on or otherwise associated with the non-electrically isolated side "S1", and the creepage distance "D1" may be provided between the second side $P_2$ of the coupler upper plate and the locations of elements (not shown) disposed on or otherwise associated with the electrically-isolated side "S2". In some embodiments, one-half of a creepage distance "D2" is provided between the third and fourth sides $P_3$ and $P_4$, respectively, of the coupler upper plate and the locations of elements (not shown) disposed or otherwise associated with lateral portions of the printed circuit board 1000.

Figure 11:
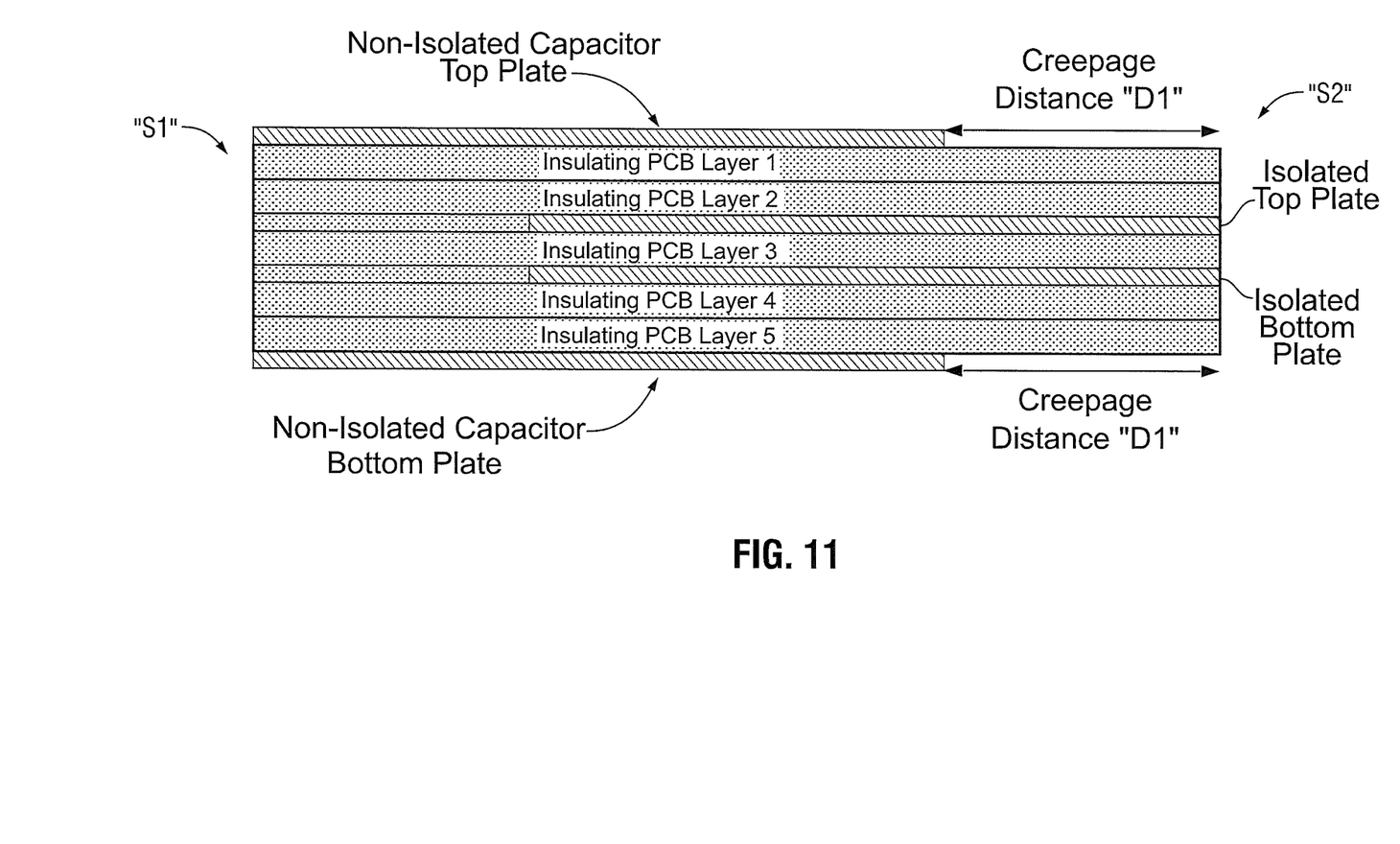
FIG. 11 is an enlarged side view of the printed circuit board including an electric-field capacitive coupler, such as the electric-field capacitive coupler shown in FIG. 10, according to an embodiment of the present disclosure.

FIG. 11 shows a side view of an electric-field capacitive coupler, such as the electric-field capacitive coupler 1024 shown in FIG. 10. In some embodiments, two insulating layers (e.g., insulating PCB layer 1 and insulating PCB layer 2 shown in FIG. 11) are provided between a non-electrically isolated capacitor top plate and an electrically-isolated top plate of the electric-field capacitive coupler, e.g., to provide electrical isolation in case of single point insulative failure. In some embodiments, two insulating layers (e.g., insulating PCB layer 4 and insulating PCB layer 5 shown in FIG. 11) are provided between a non-electrically isolated capacitor bottom plate and an electrically-isolated bottom plate of the electric-field capacitive coupler, e.g., to provide electrical isolation in case of single point insulative failure.

In the above-described embodiments, signals indicative of user input for controlling one or more operating parameters of an electrosurgical power generating source and/or at least some of the information monitored by one or more sensors, e.g., radiation detector and/or fluid-flow monitoring system, operably associated with the handpiece of a medical device may be transmitted across an electric-field capacitive coupler of the presently-disclosed electric-field capacitive coupler module.

Although embodiments have been described in detail with reference to the accompanying drawings for the purpose of illustration and description, it is to be understood that the inventive processes and apparatus are not to be construed as limited thereby. It will be apparent to those of ordinary skill in the art that various modifications to the foregoing embodiments may be made without departing from the scope of the disclosure.

What is claimed is:

1. An electric-field capacitive coupler module, comprising:
    a first processing unit;
    a first communication interface coupled to the first processing unit;
    a second communication interface; and
    an electric-field capacitive coupler apparatus, embedded in a multi-layer printed circuit board (PCB), that defines an isolation barrier coupled between the first communication interface and the second communication interface, the electric-field capacitive coupler apparatus including a first portion configured to electrically-coupled to a receiver and a second portion configured to electrically-coupled to a driver, the first portion including a first electrically-conductive plate disposed on a first layer of the PCB and a second electrically-conductive plate disposed on a second layer of the PCB.

2. The electric-field capacitive coupler module according to claim 1, further comprising an analog-to-digital converter coupled to the first processing unit.

3. The electric-field capacitive coupler module according to claim 2, wherein the analog-to-digital converter is configured to receive an analog electrical signal from a handpiece and generate a digital output signal to be provided to the first processing unit.

4. The electric-field capacitive coupler module according to claim 1, wherein the second communication interface is coupled to a second processing unit.

5. The electric-field capacitive coupler module according to claim 4, wherein the second processing unit is operably associated with a generator assembly.

6. The electric-field capacitive coupler module according to claim 5, wherein the second processing unit is disposed within the generator assembly.

7. The electric-field capacitive coupler module according to claim 1, wherein the second portion of the electric-field capacitive coupler apparatus includes a third electrically-conductive plate disposed on a third layer of the PCB and a fourth electrically-conductive plate disposed on a fourth layer of the PCB.

8. A system for transmitting data across a patient isolation barrier, the system comprising:
    a handpiece including a surgical instrument;
    a control assembly coupled to the handpiece; and
    an electric-field capacitive coupler module, including:
        a first processing unit;
        a first communication interface coupled to the first processing unit;
        a second communication interface; and
        an electric-field capacitive coupler, embedded in a multi-layer printed circuit board (PCB), that defines an isolation barrier coupled between the first communication interface and the second communication interface, the electric-field capacitive coupler apparatus including a first portion configured to electrically-coupled to a receiver and a second portion configured to electrically-coupled to a driver, the first portion including a first electrically-conductive plate disposed on a first layer of the PCB and a second electrically-conductive plate disposed on a second layer of the PCB.

9. The system according to claim 8, wherein the control assembly is configured to transmit an analog electrical signal indicative of user input.

10. The system according to claim 8, further comprising a sensor associated with the handpiece configured to transmit an analog electrical signal indicative of a sensed condition of the surgical instrument.

11. The system according to claim 8, wherein the second portion of the electric-field capacitive coupler apparatus includes a third electrically-conductive plate disposed on a third layer of the PCB and a fourth electrically-conductive plate is disposed on a fourth layer of the PCB.

* * * * *